(12) United States Patent
Fujikawa et al.

(10) Patent No.: US 6,548,813 B1
(45) Date of Patent: Apr. 15, 2003

(54) OBJECT-TO-BE-PRINTED DETECTOR AND PRINT DETECTING METHOD

(75) Inventors: Kazuhiko Fujikawa, Kyoto (JP); Takeshi Masutani, Osaka (JP); Koji Nomura, Osaka (JP); Junji Kajiwara, Osaka (JP); Yasuhiko Yokota, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/647,709

(22) PCT Filed: Feb. 2, 2000

(86) PCT No.: PCT/JP00/00551

§ 371 (c)(1),
(2), (4) Date: Feb. 28, 2001

(87) PCT Pub. No.: WO00/46033

PCT Pub. Date: Aug. 10, 2000

(30) Foreign Application Priority Data

Feb. 4, 1999 (JP) .......................................... 11/027583
Nov. 5, 1999 (JP) .......................................... 11/315192

(51) Int. Cl.[7] .............................. G01J 1/00; G01J 5/00; B41J 11/42
(52) U.S. Cl. ............................... 250/341.6; 250/341.1; 250/339.01
(58) Field of Search .......................... 250/341.6, 341.1, 250/339.01, 339.1

(56) References Cited

U.S. PATENT DOCUMENTS

| | | | | |
|---|---|---|---|---|
| 3,973,122 A | * | 8/1976 | Goldberg | 250/338.1 |
| 4,631,406 A | * | 12/1986 | Nakata | 250/338.1 |
| 4,766,316 A | * | 8/1988 | Jungkman | 250/338.3 |
| 5,434,411 A | * | 7/1995 | Miyahara et al. | 250/339.07 |
| 6,013,915 A | * | 1/2000 | Watkins | 250/341.1 |
| 6,059,406 A | * | 5/2000 | Richtsmeier et al. | 347/102 |
| 6,281,498 B1 | * | 8/2001 | Fellows | 250/339.01 |
| 6,322,192 B1 | * | 11/2001 | Walker | 347/19 |

FOREIGN PATENT DOCUMENTS

| | | | | |
|---|---|---|---|---|
| DE | 2 317 992 | | 10/1973 | |
| JP | 50-70076 | | 6/1975 | |
| JP | 58-153106 | | 9/1983 | |
| JP | 59-57107 | | 4/1984 | |
| JP | 5-16462 | | 1/1993 | |
| JP | 6-90146 | | 11/1994 | |
| JP | 10-291690 | | 11/1998 | |
| WO | WO 9822806 A1 | * | 5/1998 | G01N/21/35 |

* cited by examiner

Primary Examiner—Constantine Hannaher
Assistant Examiner—Albert Gagliardi
(74) Attorney, Agent, or Firm—McDermott, Will & Emery

(57) ABSTRACT

The present invention relates to an apparatus for detecting an object-to-be-printed and aims at providing an apparatus for detecting an object-to-be-printed which is capable of discriminating whether the object-to-be-printed is plain paper or special paper. The apparatus includes an infrared sensor for detecting infrared rays 4 radiated by heating the object-to-be-printed 1 with heating means 2 and is capable of discriminating whether the object-to-be-printed is plain paper or special paper.

28 Claims, 6 Drawing Sheets

OBJECT-TO-BE-PRINTED DETECTOR AND PRINT DETECTING METHOD

FIELD OF THE INVENTION

The present invention relates to apparatuses and methods for detecting objects-to-be-printed.

BACKGROUND OF THE INVENTION

In association with the trend in recent years toward use of color printers and higher picture-quality printing, as the objects-to-be-printed, paper of which the surface has been processed with some coating, or special types of paper of which the base material itself is special-purpose high-quality paper, glossy film, photographic-quality glossy film, photographic-quality glossy paper, OHP film, or back-printed film, etc., are being commercialized in addition to plain paper. As these special types of paper are expensive, development of means for discriminating them prior to printing the object-to-be-printed has been sought for in order that an operator of a computer and the like can avoid a situation of printing on a special piece of paper against the operator's will of printing on plain paper.

Previously, printing had been done by putting plain paper on one of two or more trays loaded on a printer, for example, on an upper tray, and special paper on a lower tray, and the operator selecting in advance which tray to use prior to printing.

During this process, in the event a different type of paper was mixed on a predetermined tray, the operator suffered a problem of printing on wrong paper against the will.

The present invention addresses the above described previous problem and aims at providing an apparatus and method for detecting objects-to-be-printed with which the object-to-be-printed can be distinguished as to whether it is plain paper or special paper.

SUMMARY OF THE INVENTION

In order to achieve the above object, the present invention comprises an object-to-be-printed, a heating means for heating the object-to-be-printed, and an infrared sensor for detecting infrared rays radiated by the object-to-be-printed heated by the heating means.

The present invention provides an apparatus and method for detecting an object-to-be-printed with which the object-to-be-printed can be distinguished as to whether it is plain paper or special paper.

DESCRIPTION OF THE PREFERRED EMBODIMENTS

Figure 1:
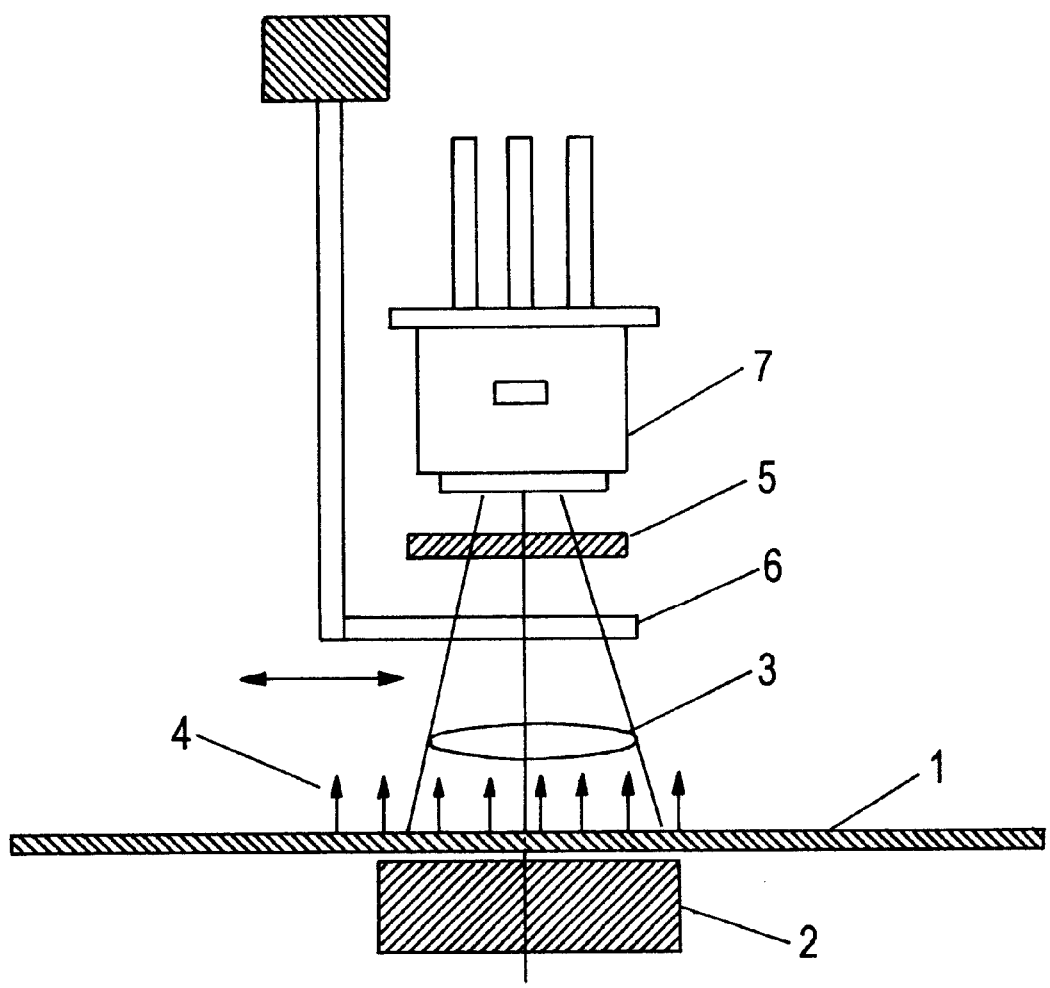
FIG. 1 is a cross-sectional view of an apparatus for detecting objects-to-be-printed in a first exemplary embodiment of the present invention.

A first aspect of the present invention comprises an object-to-be-printed, a heating means for heating the object-to-be-printed, and an infrared sensor for detecting the infrared rays radiated by the object-to-be-printed which is heated by the heating means, and has an effect of discriminating the types of object-to-be-printed by detecting the difference in the amount of infrared rays radiated by the object-to-be-printed.

Also, a second aspect is one in which a filter for selectively passing infrared rays is provided between the object-to-be-printed and the infrared sensor of the first aspect. As it is capable of detecting the difference in the spectral characteristic of the infrared rays radiated by the object-to-be-printed, it has an effect of precisely discriminating the types of object-to-be-printed.

Also, a third aspect is one in which an optical chopper for interrupting or passing infrared rays from the object-to-be-printed is provided between the object-to-be-printed and the infrared sensor in the first or second aspect. As plural number of measurements is made possible by intermittently interrupting the infrared rays from the object-to-be-printed thereby enabling detection of the difference in the amount of infrared rays with enhanced precision, it has an effect of enabling discrimination of the types of object-to-be-printed with further enhanced precision.

Also, a fourth aspect is one in which a lens for collecting infrared rays is provided between the object-to-be-printed and the infrared sensor of any one of the first to the third aspects. As the focal distance to be determined by the relation between the lens and the infrared sensor can be shortened, the heating means can be downsized, thereby presenting an effect of enabling downsizing of the overall structure.

A fifth aspect is an apparatus for detecting objects-to-be-printed as described in the second aspect and provided with a filter as described below. The filter is constituted of at least one of filters for selectively passing a wavelength band of 9.5 to 10.5 micrometer, selectively passing a wavelength band of 4.0 to 5.5 micrometer, or selectively passing a wavelength band of 2.5 to 3.5 micrometer. Being provided with this filter, it has an effect of enabling discrimination of the object-to-be-printed between plain paper and special paper with an enhanced precision.

A sixth aspect comprises an object-to-be-printed, a heating means for heating the object-to-be-printed, an infrared sensor for detecting the infrared rays radiated by the object-to-be-printed heated by the heating means, and a filter window integrally provided with the infrared sensor that selectively passes the infrared rays. By sharing a filter and a window, it has an effect of enabling downsizing at a low cost.

A seventh aspect is one in which an optical chopper for interrupting or passing infrared rays is provided between the heating means and the filter window of the sixth aspect. By intermittently interrupting the infrared rays radiated by the object-to-be-printed, plural number of measurements is made possible thereby enabling detection of the difference in the amount of infrared rays with an enhanced precision. As a result, it has an effect of enabling discrimination of the types of object-to-be-printed with further enhanced precision.

An eighth aspect is one in which a lens is provided between the heating means and the filter window of the sixth or seventh aspect for collecting infrared rays radiated by the object-to-be-printed heated by the heating means. As the focal distance to be determined by the relation between the lens and the infrared sensor can be shortened, the heating means can be downsized, thus presenting an effect of enabling downsizing of the overall structure as well.

A ninth aspect is an apparatus for detecting objects-to-be-printed as described in the sixth aspect and provided with a filter window as described below. The filter window is constituted of at least one of filter windows for selectively passing a wavelength band of 9.5 to 10.5 micrometer, selectively passing a wavelength band of 4.0 to 5.5 micrometer, or selectively passing a wavelength band of 2.5 to 3.5 micrometer. Being provided with the filter window, it has an effect of enabling discrimination of objects-to-be-printed between plain paper and special paper with an enhanced precision.

A tenth aspect comprises an object-to-be-printed, heating means for heating the object-to-be-printed, an infrared sensor for detecting the infrared rays radiated by the object-to-be-printed heated by the heating means, and a filter lens window integrated with the infrared sensor for collecting as well as selectively passing the infrared rays. By sharing a filter, a lens and a window, it has an effect of enabling downsizing at a low cost.

Also, an eleventh aspect is an apparatus for detecting objects-to-be-printed as described in the tenth aspect and provided with a filter lens window as described below. The filter lens window is constituted of at least one of filter lens windows for selectively passing a wavelength band of 9.5 to 10.5 micrometer, selectively passing a wavelength band of 4.0 to 5.5 micrometer, or selectively passing a wavelength band of 2.5 to 3.5 micrometer. Being provided with this filter lens window, it has an effect of enabling discrimination of objects-to-be-printed between plain paper and special paper with an enhanced precision.

Also, a twelfth aspect comprises an object-to-be-printed, a trapezoidal optical plate provided on one of the sides of the object-to-be-printed, a heating means provided on one of the lateral sides of the optical plate, and an infrared sensor provided on the other lateral side of the optical plate. As it is capable of detecting difference in the spectral characteristic of the infrared rays reflected by the object-to-be-printed, it has an effect of enabling discrimination of the types of object-to-be-printed with an enhanced precision.

Also, a thirteenth aspect is one in which a filter that selectively passes infrared rays is provided between the side of the optical plate opposite to the heating means and the infrared sensor of the twelfth aspect. As it is capable of detecting difference in the spectral characteristic of the infrared rays reflected by the object-to-be-printed, it has an effect of enabling discrimination of the types of object-to-be-printed with an enhanced precision.

Also, a fourteenth aspect is one in which a lens for collecting infrared rays is provided between the side of the optical plate opposite to the heating means and the infrared sensor of the twelfth or thirteenth aspect. As the focal distance determined by the relation between the lens and the infrared sensor can be shortened, the heating means can be downsized, thus presenting an effect of enabling downsizing of the overall structure as well.

Also, a fifteenth aspect is one in which the infrared sensor in any one of the first, sixth, tenth, and twelfth aspects is either pyroelectric type or thermocouple type. As the sensitivity of detecting infrared rays does not depend on the wavelength of infrared rays, it has an effect of enabling production of an output by using a filter for any band.

Also, a sixteenth aspect is one in which an object-to-be-printed is heated by a heating means and the infrared rays radiated by the object-to-be-printed are detected while the object-to-be-printed is kept in contact with the heating means. It has an effect of enabling discrimination of the types of object-to-be-printed by stably detecting the amount of difference in the infrared rays radiated by the object-to-be-printed without being affected by the surroundings by being kept in contact.

Also, a seventeenth aspect is one in which quality of paper is discriminated by detecting infrared rays having wavelength of 9.5 to 10.5 micrometer or 4.0 to 5.5 micrometer or 2.5 to 3.5 micrometer as radiated by the object-to-be-printed described in the sixteenth aspect. It has an effect of enabling discrimination of object-to-be-printed between plain paper and special paper with an enhanced precision.

Also, an eighteenth aspect is one in which the amount of moisture contained in paper can be measured by detecting infrared rays having wavelength of 2.5 to 3.5 micrometer or 5.5 to 6.5 micrometer as radiated by the object-to-be-printed described in the sixteenth aspect.

Also, a nineteenth aspect is one in which an object-to-be-printed is heated by a heating means and infrared rays radiated by the object-to-be-printed is detected after separating the object-to-be-printed from the heating means. It has an effect of enabling discrimination of the difference in the thermal time constants of the object-to-be-printed.

Also, a twentieth aspect is one in which thickness of paper is measured by detecting the wavelength of infrared rays radiated by the object-to-be-printed as described in the nineteenth aspect. It has an effect of enabling discrimination with an enhanced precision as the difference in the thermal time constants due to the difference in the thickness of the objects-to-be-printed is measured.

Operation of the apparatus for detecting objects-to-be-printed and the method for detecting objects-to-be-printed as configured above will now be described.

To begin with, referring to drawings, an apparatus for detecting an object-to-be-printed in the first exemplary embodiment of the present invention will be described.

FIG. 1 is a cross-sectional view of an apparatus for detecting an object-to-be-printed in the first exemplary embodiment of the present invention.

In the drawing, an object-to-be-printed 1 is plain paper or special paper. A heating means 2, comprising a ceramic heater, halogen lamp, or the like provided either in contact with or at some distance from the bottom surface of the object-to-be-printed 1, is heated to approximately 160 to 180 degrees C. to heat the object-to-be-printed 1 to approximately 80 degrees C. A lens 3 made of silicon, polyethylene, or the like is provided above the object-to-be-printed 1 for collecting infrared rays 4 radiated by the object-to-be-printed 1 heated by the heating means 2. A filter 5 comprising at least one of filters for selectively passing 9.5 to 10.5 micrometer wavelength band, selectively passing 4.0 to 5.5 micrometer wavelength band, or selectively passing 2.5 to 3.5 micrometer wavelength band is provided above the lens 3. Also, between the filter 5 and the lens 3, an optical chopper 6 made of stainless steel, iron-nickel steel, iron-nickel-cobalt steel, and the like is provided for interrupting or passing the infrared rays 4. An infrared sensor 7 for detecting the infrared rays 4 that have passed the optical chopper 6 is provided above the optical chopper 6.

Figure 2:
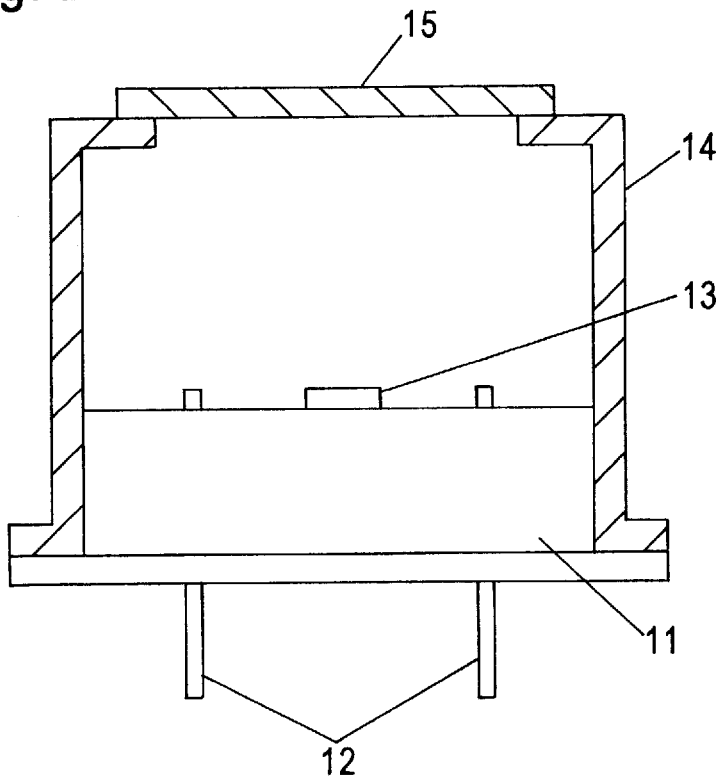
FIG. 2 is a cross-sectional view of an infrared sensor, being a key part of the apparatus for detecting objects-to-be-printed.

The infrared sensor 7 is configured in the way illustrated in FIG. 2. In FIG. 2, a mount 11 has lead electrodes 12. An infrared ray detecting unit 13 consisting of a thin film or the like made by adding lanthanum to lead titanate, which has a function of absorbing infrared rays, and electrically connected to the lead electrodes 12 is provided on the top surface of the mount 11. A cylindrical sealing member 14 made of iron, Kovar, or the like is provided on the sides of the mount 11 in a manner such that it covers at least the infrared ray detecting unit 13. The pyroelectric infrared sensor 7 is configured in such a way that an infrared ray incident window 15 made of silicon, germanium, or the like is provided to cover an opening of the sealing member 14. Although surface charges always appear in the infrared sensor 7 due to spontaneous polarization, in the steady state in the atmosphere, it remains electrically neutral as the surface charges combine with charges in the atmosphere. When infrared rays 4 enter the infrared sensor 7, the temperature changes, causing a change in the neutral state of the charge conditions. The amount of incident infrared rays is measured by detecting the charges that appear during this change.

A description of the method of detection will now be given below on the apparatus for detecting an object-to-be-printed as configured above.

To begin with, the object-to-be-printed 1 is laid above the heating means 2, and the object-to-be-printed 1 is heated up to about 80 degrees C. by heating the heating means 2 to about 160 degrees C. to 180 degrees C.

Subsequently, the infrared rays 4 collected by the lens 3 are led to the filter 5 by opening the optical chopper 6. Normally, the optical chopper 6 is closed to the filter 5 and is opened only when to detect the infrared rays 4.

Next, the filter 5 allows only those infrared rays 4 to pass that satisfy the conditions of the filter 5 as described below.

Finally, the type of the object-to-be-printed 1 is identified by detecting the amount of infrared rays that have passed the filter 5 and arrived at the infrared sensor 7.

Referring to drawings and taking plain paper and special paper as examples of the object-to-be-printed, a description will be given in the following on the spectral characteristic based on the relation between the wavelength of the infrared rays radiated by the object-to-be-printed 1 heated by the heating means 2 and the radiation rate.

Figure 3:
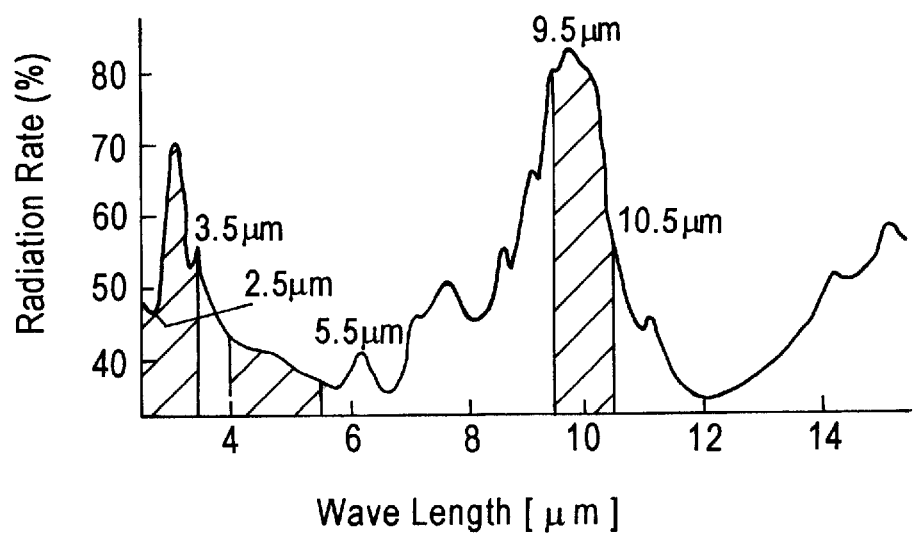
FIG. 3 is a graph illustrating spectral characteristic in terms of the relation between wavelength of infrared rays from plain paper heated by a heating means, being a key part of the apparatus for detecting objects-to-be-printed, and the radiation rate.
Figure 4:
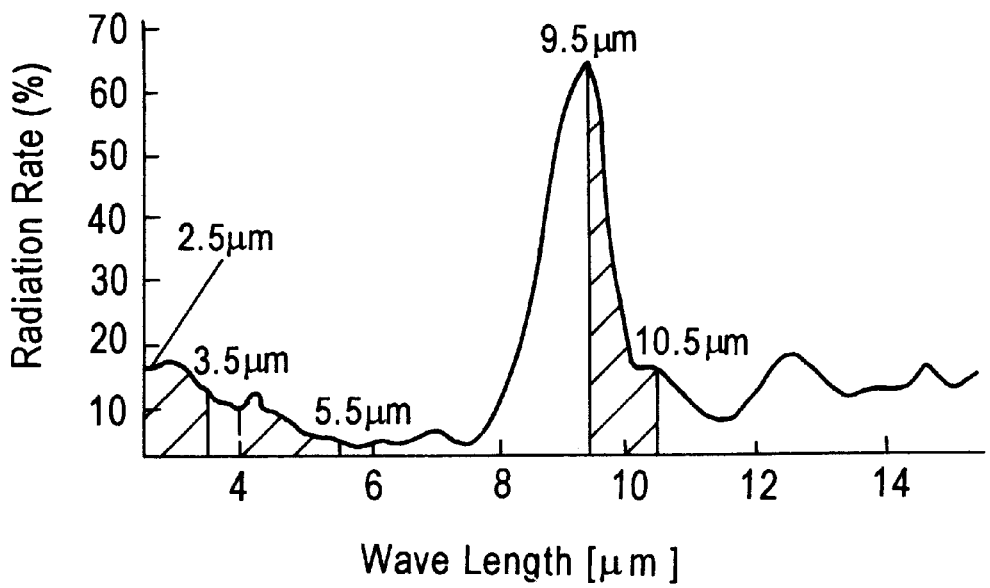
FIG. 4 is a graph illustrating spectral characteristic in terms of the relation between wavelength of the infrared rays from special paper heated by the heating means, being a key part of the apparatus for detecting objects-to-be-printed, and the radiation rate.

FIG. 3 is a graph illustrating the spectral characteristic of plain paper based on the relation between the wavelength of the infrared rays from the plain paper heated by the heating means, being an essential part of the apparatus for detecting an object-to-be-printed in the first exemplary embodiment of the present invention, and the radiation rate. FIG. 4 is a graph illustrating the spectral characteristic of special paper based on the relation between the wavelength of the infrared rays from the special paper heated by the heating means, being an essential part of the apparatus for detecting an object-to-be-printed, and the radiation rate.

While the radiation rate of the plain paper shown in FIG. 3 is from about 60% to 85% in the wavelength passband of 9.5 to 10.5 micrometers, that of the special paper shown in FIG. 4 is from about 15% to 60%. Discrimination as to whether the paper is plain paper or special paper is made based on the difference in the radiation rates of the plain paper and special paper. As has been described above, by using a filter 5 having a wavelength passband of 9.5 to 10.5 micrometers, efficient discrimination between plain paper and special paper is enabled.

Also, while the radiation rate of the plain paper shown in FIG. 3 is from about 37% to 43% in the wavelength passband of 4.0 to 5.5 micrometers, that of the special paper shown in FIG. 4 is from about 5% to 10%. In the same manner as above, discrimination as to whether the paper is plain paper or special paper is made based on the difference in the radiation rates of the plain paper and the special paper. As has been described above, by using a filter 5 having a wavelength passband of 4.0 to 5.5 micrometers, efficient discrimination between plain paper and special paper is enabled.

Also, while the radiation rate of the plain paper shown in FIG. 3 is from about 15% to 20% in the wavelength passband of 2.5 to 3.5 micrometers, that of the special paper shown in FIG. 4 is from about 55% to 70%. In the same manner as above, discrimination as to whether the paper is plain paper or special paper is made based on the difference in the radiation rates of the plain paper and the special paper. As has been described above, by using a filter 5 having a passband of 2.5 to 3.5 micrometers, efficient discrimination between plain paper and special paper is enabled.

In this exemplary embodiment, although a description was made based on a pyroelectric infrared sensor, a thermocouple type infrared sensor will also do. A thermocouple type infrared sensor is suitable as it allows high precision measurement even when no chopper is available. A pyroelectric type infrared sensor is suitable as it allows high precision measurement because five to ten times as high S/N ratio as that of the thermocouple type is obtainable.

Also, though the configuration in this exemplary embodiment comprised a lens, an optical chopper, and a filter, these may be selectively combined as required.

Figure 5:
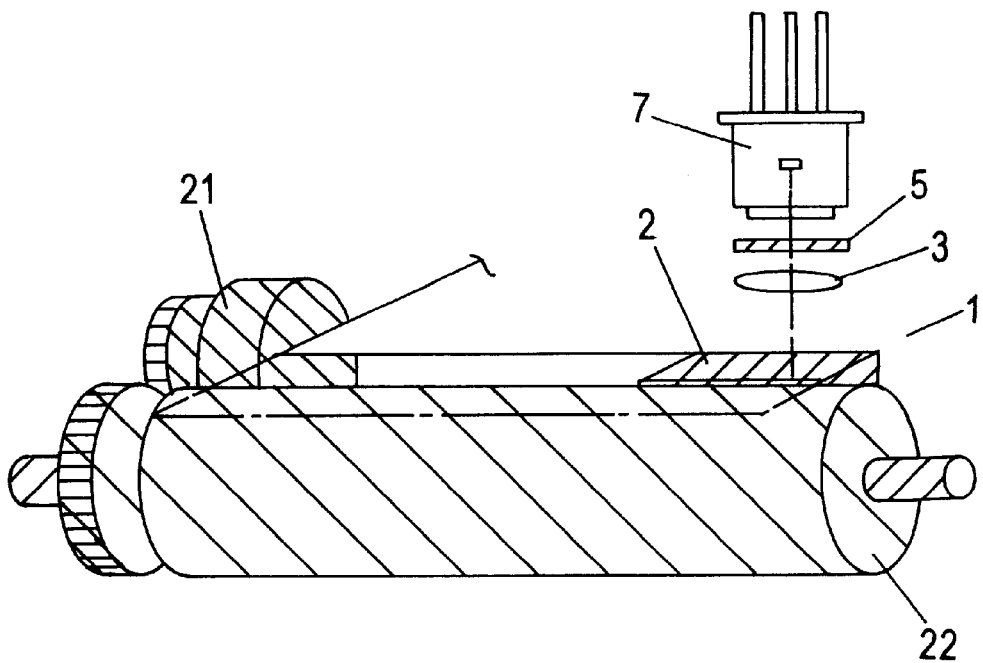
FIG. 5 is a perspective view of a paper transfer mechanism of a bubble-jet printer to illustrate the embodiment.

Also, when to use the apparatus for detecting an object-to-be-printed in proximity to the paper transport mechanism inside a bubble-jet printer, the heating means 2 may be disposed, as shown in FIG. 5, close to a paper feed roller 22 which is driven by a motor 21 to be used for feeding paper so that infrared rays 4 from the object-to-be-printed 1 may be collected with the lens 3 as the object-to-be-printed 1 passes above the heating means 2, and detected by the infrared sensor 7 after selectively passing through the filter 5. In this case, the lens 3 and the filter 5 may be used upon selection if need be, and the optical chopper 6 (not shown in the drawing) may be omitted by combining, as the motion of the object-to-be-printed 1 that passes the heating means 2, a forward motion in the direction of transport and a reverse motion in the direction opposite to the direction of transport.

Figure 6:
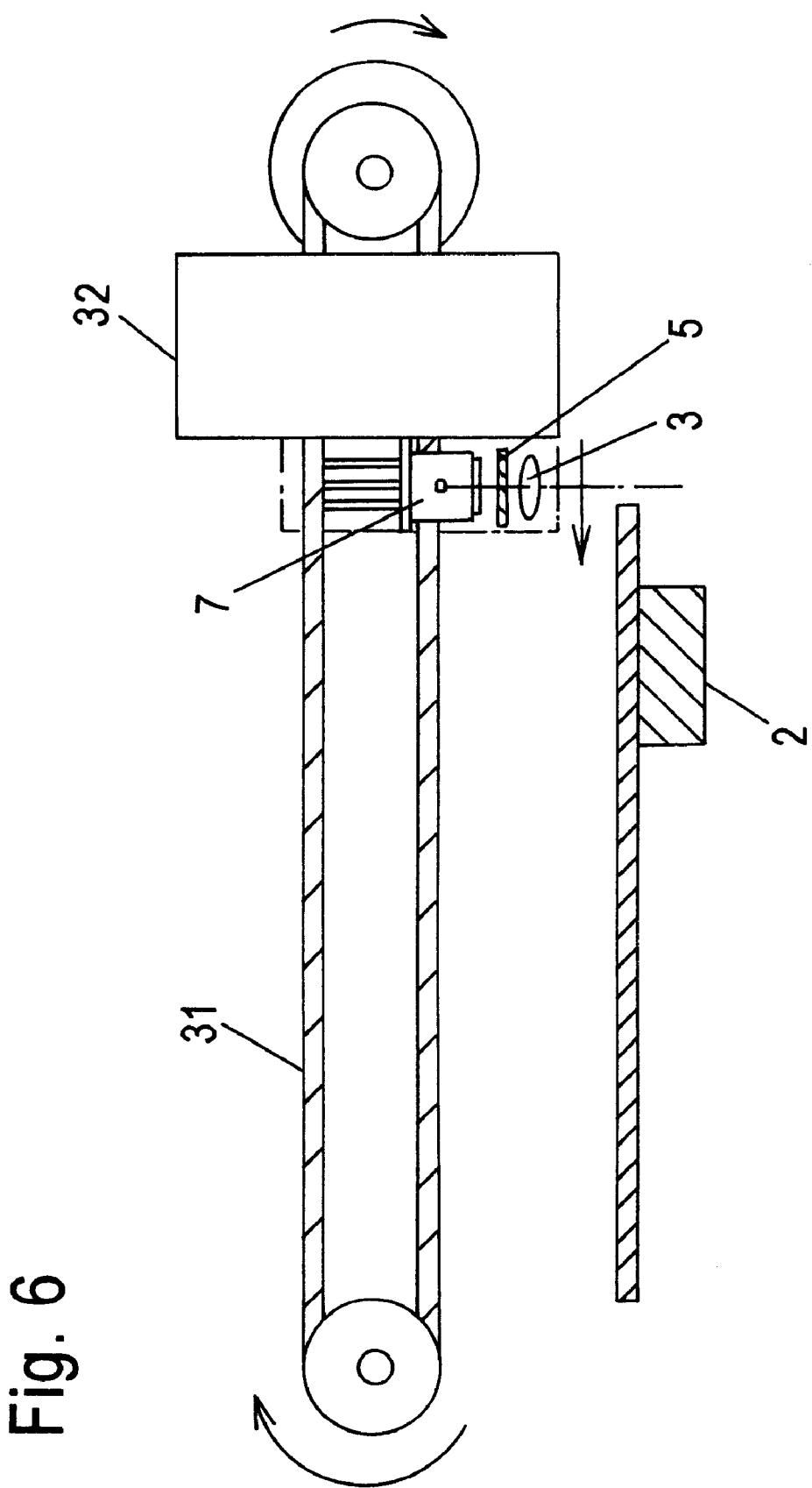
FIG. 6 is a front view of a printing mechanism of a bubble-jet printer to illustrate the embodiment.

Also, when to use the apparatus for detecting an object-to-be-printed in proximity to the printing mechanism inside a bubble-jet printer, the infrared sensor 7 may be integrally provided, as illustrated in FIG. 6, on a printing head (not shown in the drawing) which is moved by a belt 31 when printing and on a printing carriage 32 which supplies ink (not shown in the drawing) to the printing head, and the heating means 2 may be provided underneath the object-to-be-printed 1 so that infrared rays 4 from the object-to-be-printed 1 can be collected by the lens 3 when the object-to-be-printed 1 passes above the heating means 2, selectively passed through the filter 5, and detected by the infrared sensor 7. In this case, the lens 3 and the filter 5 may be used upon selection if need be, and the optical chopper 6 (not shown in the drawing) may be omitted if the apparatus is so designed that infrared rays 4 can be detected when the infrared sensor 7 moves above the heating means 2.

Next, referring to a drawing, a description will be given on an apparatus for detecting an object-to-be-printed in the second exemplary embodiment of the present invention.

Figure 7:
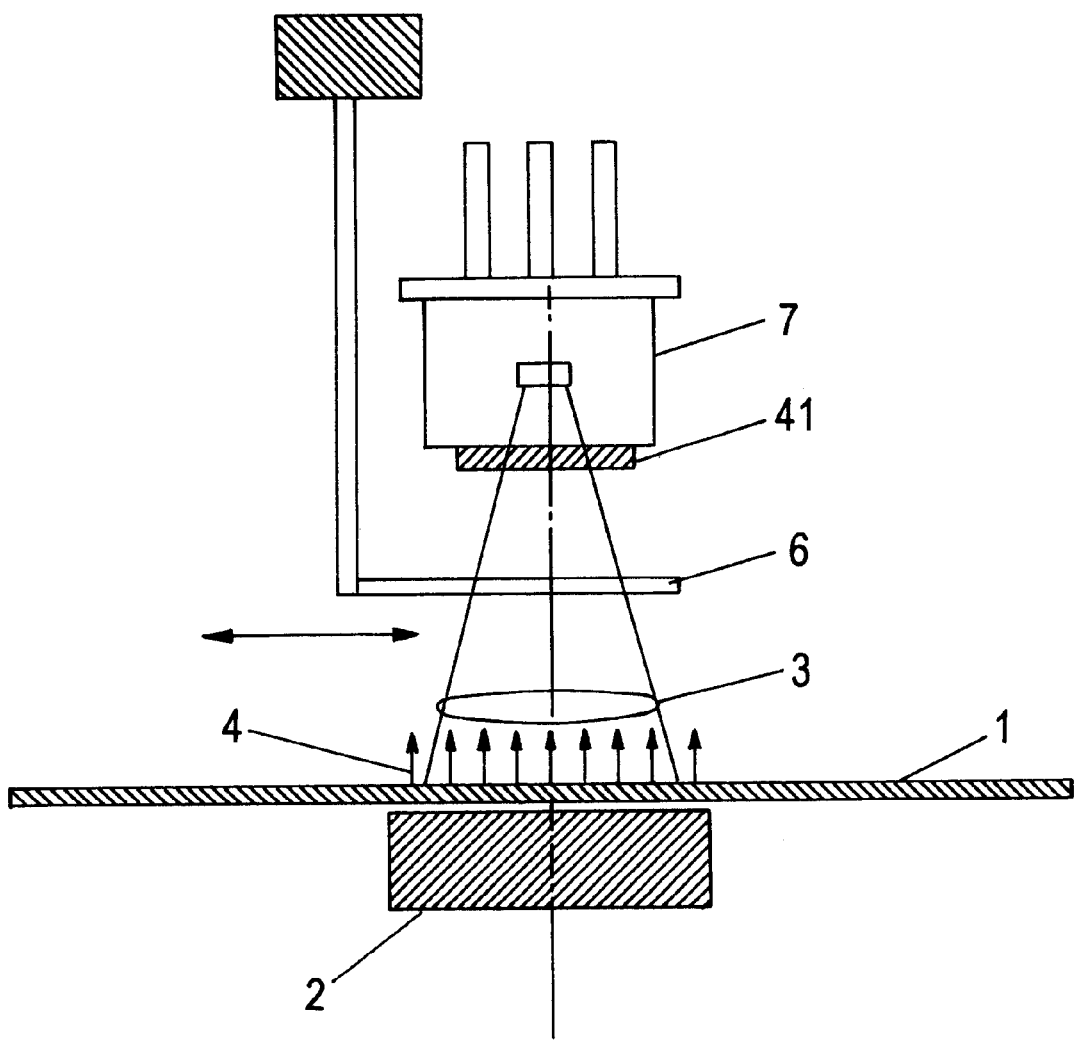
FIG. 7 is a cross-sectional view of an apparatus for detecting objects-to-be-printed in a second exemplary embodiment of the present invention.

FIG. 7 is a cross-sectional view of the apparatus for detecting an object-to-be-printed in the second exemplary embodiment of the present invention. Structural components which are identical as shown in FIG. 1 explained in the first exemplary embodiment are indicated by the same reference numerals and detail description will be omitted.

A heating means 2 is provided underneath an object-to-be-printed 1 in contact with or apart from it. A lens 3 is provided above the object-to-be-printed 1 for collecting infrared rays 4 radiated by the object-to-be-printed 1 heated by the heating means 2. An optical chopper 6 for interrupting or passing the infrared rays 4 is provided above the lens 3. A filter window 41 comprising at least one of filter windows for selectively passing a wavelength band of 9.5 to 10.5 micrometer, selectively passing a wavelength band of 4.0 to 5.5 micrometer, or selectively passing a wavelength band of 2.5 to 3.5 micrometer of the infrared rays 4 passed by the optical chopper 6 is provided integrally with the infrared sensor 7 for detecting the infrared rays 4.

By configuring the filter window 41 into an integral unit with the infrared sensor 7, a filter and a window can be shared thus presenting an effect of enabling downsizing at a low cost.

In this exemplary embodiment, although the apparatus for detecting an object-to-be-printed comprised a lens, an optical chopper and a filter, these may be used in selected combination as required.

Now, referring to a drawing, a description will be given on an apparatus for detecting an object-to-be-printed in the third exemplary embodiment of the present invention.

Figure 8:
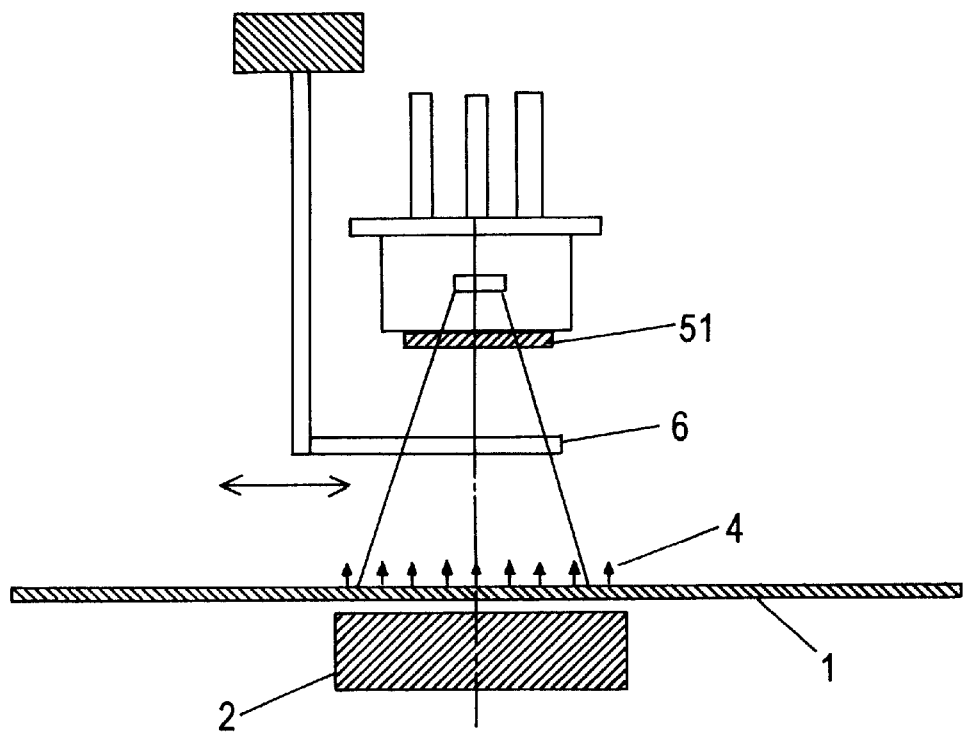
FIG. 8 is a cross-sectional view of an apparatus for detecting objects-to-be-printed in a third exemplary embodiment of the present invention.

FIG. 8 is a cross-sectional view of the apparatus for detecting an object-to-be-printed in the third exemplary embodiment of the present invention. Structural components which are identical as in FIG. 1 in the first exemplary embodiment are indicated by the same reference numerals and detail description will be omitted.

A heating means 2 is provided underneath an object-to-be-printed 1 in contact with or apart from it. An optical chopper 6 is provided above the object-to-be-printed 1 for interrupting or passing infrared rays 4 radiated by the object-to-be-printed 1 heated by the heating means 2. A filter lens window 51 for collecting the infrared rays 4 passed by the optical chopper 6 and comprising at least one of filter lens windows for selectively passing a wavelength band of 9.5 to 10.5 micrometer, selectively passing a wavelength band of 4.0 to 5.5 micrometer, or selectively passing a wavelength band of 2.5 to 3.5 micrometer of the infrared rays 4 passed by the optical chopper 6 is provided above the optical chopper 6 integrally with the infrared sensor 7.

By configuring the filter lens window 51 into an integral unit with the infrared sensor 7, a filter, a lens and a window can be shared thus presenting an effect of downsizing at a low cost.

In this exemplary embodiment, although the apparatus for detecting an object-to-be-printed comprised a lens, an optical chopper, and a filter, these may be used in selected combination as required.

Now, referring to a drawing, a description will be given on an apparatus for detecting an object-to-be-printed in the fourth exemplary embodiment of the present invention.

Figure 9:
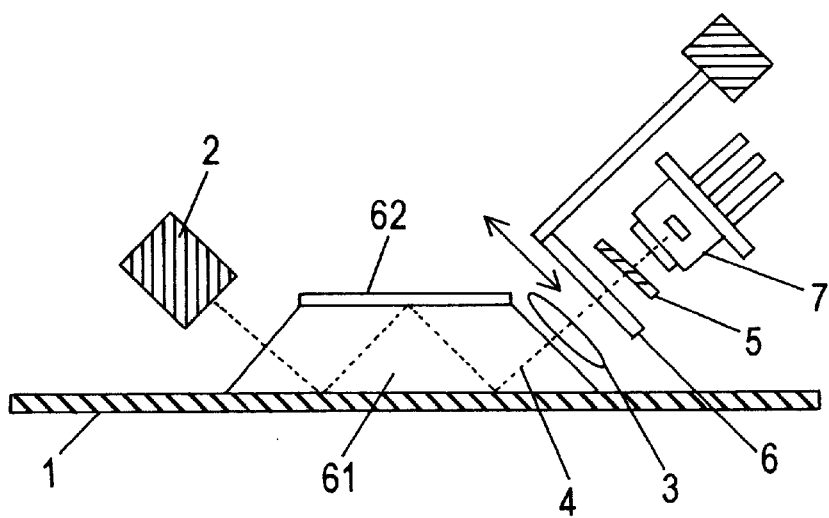
FIG. 9 is a front view of an apparatus for detecting objects-to-be-printed in a fourth exemplary embodiment of the present invention.

FIG. 9 is a front view of an apparatus for detecting an object-to-be-printed in the fourth exemplary embodiment of the present invention. Structural components which are identical as in FIG. 1 in the first exemplary embodiment are indicated by the same reference numerals and detail description will be omitted.

A trapezoidal optical plate 61 made of silicon, germanium or chalcogenide materials such as zinc sulfur and the like, is provided on the top surface of an object-to-be-printed 1. And the optical plate 61 has, on its upper bottom surface which is in parallel to the object-to-be-printed 1, a reflecting film 62 made of aluminum, gold, copper, or the like. Also, a heating means 2 is provided spaced apart from and perpendicular to one side of the optical plate 61 to supply radiated infrared rays 4 into the optical plate 61. An optical chopper 6 is provided spaced apart from and perpendicular to the other side of the optical plate 61 for interrupting or passing infrared rays 4 radiated by the heating means 2 and reflected sequentially in the order of the object-to-be-printed 1, the reflecting film 62, and the object-to-be-printed 1. A filter 5 comprising at least one of filters for selectiely passing a wavelength band of 9.5 to 10.5 micrometer, selectively passing a wavelength band of 4.0 to 5.5 micrometer, or selectively passing a wavelength band of 2.5 to 3.5 micrometer is provided above the optical chopper 6. An infrared sensor 7 is provided above the filter 5 for detecting infrared rays 4 that have passed the optical chopper 6.

In this exemplary embodiment, although reference was made to the use of a pyroelectric infrared sensor, a thermocouple type infrared sensor will also do. A thermocouple type infrared sensor is suitable as it allows high precision measurement even when no chopper is in use. A pyroelectric type infrared sensor is suitable as it allows high precision measurement because of five to ten times as high S/N ratio as that of the thermocouple type.

In this exemplary embodiment, although the apparatus for detecting an object-to-be-printed comprised a lens, an optical chopper and a filter, these may be used in selected combination as required.

Also, in the above described first to the fourth exemplary embodiments, quality of paper is discriminated by detecting infrared rays radiated by the object-to-be-printed; however, quantity of moisture in the object-to-be-printed such as paper can be measured by using similar apparatus.

In this case, the infrared rays radiated by the object-to-be-printed are 2.5 to 3.5 micrometer or 5 to 6.5 micrometer in wavelength, which are radiation bands of water. When compared with a dry object-to-be-printed, a moist object-to-be-printed shows greater amount of radiation in each of the above bands. In other words, radiation corresponding to the quantity of moisture in the object-to-be-printed is made, and, by detecting the amount of radiation, the quantity of moisture of the object-to-be-printed can be measured.

A description of an apparatus for detecting an object-to-be-printed in the fifth exemplary embodiment of the present invention will be given in the following.

To begin with, an object-to-be-printed is laid on a heating means, and the heating means is separated from the object-to-be-printed after it has been heated up to about 80 degree C. by heating the heating means to about 160 to 180 degree C.

Subsequently, infrared rays radiated by the heated object-to-be-printed is collected with a lens if necessary.

Next, the infrared rays collected by the lens are transferred to a filter by opening the optical chopper if necessary. Normally, the optical chopper is closed to the filter and is opened only when to detect infrared rays.

Finally, the quantity of infrared rays that have passed the filter and arrived at an infrared sensor is detected to measure thickness of the object-to-be-printed.

In this case, when the change of sensor output is measured from the moment the heating means is separated, the rate of change is different depending on the thickness of the object-to-be-printed. Namely, as the thickness increases, the rate of change decreases, or the thermal time constant increases. By detecting the difference in the thermal time constants, it is possible to measure the thickness of the object-to-be-printed. Here, change in the output was measured after heating the object-to-be-printed and then separating the heating means; however, it goes without saying that similar effect can be obtained by measuring the change of output from the moment the object-to-be-printed is brought into intimate contact with or close to the heating means.

The apparatus for detecting an object-to-be-printed and the method for detecting an object-to-be-printed in the first to the fifth exemplary embodiments can be used in printers. It goes without saying that the printers include ink-jet printers, laser printers, and copying machines.

INDUSTRIAL APPLICATION

As has been described above, the present invention has an effect of providing an apparatus for detecting an object-to-be-printed which is capable of discriminating whether the object-to-be-printed is plain paper or special paper.

What is claimed is:

1. An apparatus for detecting an object-to-be-printed comprising an object-to-be-printed, heating means for heating the object-to-be-printed, and an infrared sensor for detecting infrared rays radiated by the object-to-be-printed heated by the heating means,
   wherein said apparatus determines the type of object being heated based on the presence or absence of said radiated infrared rays within a predefined frequency band.

2. The apparatus for detecting an object-to-be-printed of claim 1, wherein a filter that selectively passes infrared rays is provided between the object-to-be-printed and the infrared sensor.

3. The apparatus for detecting an object-to-be-printed of claim 2, wherein the filter comprises at least one of a filter that selectively passes 9.5 to 10.5 micrometer wavelength band, a filter that selectively passes 4.0 to 5.5 micrometer wavelength band, and a filter that selectively passes 2.5 to 3.5 micrometer wavelength band.

4. The apparatus for detecting an object-to-be-printed of claim 2, wherein an optical chopper that interrupts or passes infrared rays from the object-to-be-printed is provided between the object-to-be-printed and the infrared sensor.

5. The apparatus for detecting an object-to-be-printed of claim 2, wherein a lens for collecting infrared rays is provided between the object-to-be-printed and the infrared sensor.

6. The apparatus for detecting an object-to-be-printed of claim 1, wherein an optical chopper that interrupts or passes infrared rays from the object-to-be-printed is provided between the object-to-be-printed and the infrared sensor.

7. The apparatus for detecting an object-to-be-printed of claim 6, wherein a lens for collecting infrared rays is provided between the object-to-be-printed and the infrared sensor.

8. The apparatus for detecting an object-to-be-printed of claim 1, wherein a lens for collecting infrared rays is provided between the object-to-be-printed and the infrared sensor.

9. An apparatus for detecting an object-to-be-printed of claim 1, wherein the infrared sensor is of either pyroelectric type or thermocouple type.

10. An apparatus for detecting an object-to-be-printed comprising an object-to-be-printed, heating means for heating the object-to-be-printed, an infrared sensor for detecting infrared rays radiated by the object-to-be-printed heated by the heating means, and a filter window which is integrated with the infrared sensor and which selectively passes the infrared rays,
    wherein said apparatus determines the type of object being heated based on the presence or absence of said radiated infrared rays within a predefined frequency band.

11. The apparatus for detecting an object-to-be-printed of claim 10, wherein an optical chopper for interrupting or passing infrared rays is provided between the heating means and the filter window.

12. The apparatus for detecting an object-to-be-printed of claim 11, wherein a lens for collecting infrared rays radiated by the object-to-be-printed heated by the heating means is provided between the the heating means and the filter window.

13. The apparatus for detecting an object-to-be-printed of claim 10, wherein a lens for collecting infrared rays radiated by the object-to-be-printed heated by the heating means is provided between the heating means and the filter window.

14. The apparatus for detecting an object-to-be-printed of claim 10, wherein the filter window comprises at least one of a filter window that selectively passes 9.5 to 10.5 micrometer wavelength band, a filter window that selectively passes 4.0 to 5.5 micrometer wavelength band, and a filter window that selectively passes 2.5 to 3.5 micrometer wavelength band.

15. An apparatus for detecting an object-to-be-printed of claim 10, wherein the infrared sensor,is of either pyroelectric type or thermocouple type.

16. An apparatus for detecting an object-to-be-printed comprising an object-to-be-printed, heating means for heating the object-to-be-printed, an infrared sensor for detecting infrared rays radiated by the object-to-be-printed heated by the heating means, and a filter lens window integrated with the infrared sensor for collecting and selectively passing the infrared rays,
    wherein said apparatus determines the type of object being heated based on the presence or absence of said radiated infrared rays within a predefined frequency band.

17. The apparatus for detecting an object-to-be-printed of claim 16, wherein the filter lens window comprises at least one of a filter lens window that selectively passes 9.5 to 10.5 micrometer wavelength band, a filter lens window that selectively passes 4.0 to 5.5 micrometer wavelength band, and a filter lens window that selectively passes 2.5 to 3.5 micrometer wavelength band.

18. An apparatus for detecting an object-to-be-printed of claim 16, wherein the infrared sensor is of either pyroelectric type or thermocouple type.

19. An apparatus for detecting an object-to-be-printed comprising an object-to-be-printed, a trapezoidal optical plate provided on one of the surfaces of the object-to-be-printed, heating means provided on one side of the optical plate, and an infrared sensor provided on the other side of the optical plate.

20. An apparatus for detecting an object-to-be-printed of claim 19, wherein a filter for selectively passing infrared rays is provided between the side of the optical plate opposite to the heating means and the infrared sensor.

21. An apparatus for detecting an object-to-be-printed of claim 20, wherein a lens for collecting infrared rays is provided between the side of the optical plate opposite to the heating means and the infrared sensor.

22. An apparatus for detecting an object-to-be-printed of claim 19, wherein a lens for collecting infrared rays is provided between the side of the optical plate opposite to the heating means and the infrared sensor.

23. An apparatus for detecting an object-to-be-printed of claim 19, wherein the infrared sensor is of either pyroelectric type or thermocouple type.

24. A method for detecting an object-to-be-printed by heating the object-to-be-printed with heating means and detecting infrared rays radiated by the object-to-be-printed with the object-to-be-printed made in contact with the heating means, wherein said method determines the type of object being heated based on the presence or absence of said radiated infrared rays within a predefined frequency band.

25. The method for detecting an object-to-be-printed of claim 24, wherein paper quality is discriminated by detecting infrared rays having wavelength of any of 9.5 to 10.5 micrometer, 4.0 to 5.5 micrometer, or 2.5 to 3.5 micrometer radiated by the object-to-be-printed.

26. The method for detecting an object-to-be-printed of claim 24, wherein the amount of moisture contained in the paper is measured by detecting infrared rays having wavelength of either 2.5 to 3.5 micrometer or 5.5 to 6.5 micrometer radiated by the object-to-be-printed.

27. A method for detecting an object-to-be-printed by heating the object-to-be-printed with heating means and detecting the infrared rays radiated by the object-to-be-printed after the object-to-be-printed is separated from the heating means, wherein said method determines the type of object being heated based on the presence or absence of said radiated infrared rays within a predefined frequency band.

28. The method for detecting an object-to-be-printed of claim 27, wherein thickness of paper is measured by detecting wavelength of infrared rays radiated by the object-to-be-printed.

* * * * *

UNITED STATES PATENT AND TRADEMARK OFFICE
CERTIFICATE OF CORRECTION

PATENT NO. : 6,548,813 B1 Page 1 of 1
DATED : April 15, 2003
INVENTOR(S) : Kazuhiko Fujikawa et al.

It is certified that error appears in the above-identified patent and that said Letters Patent is hereby corrected as shown below:

Title page,
Item [56] References Cited, U.S. PATENT DOCUMENTS, above "3,973,122", insert
-- 3,043,956 A   7/1962  Cohen --; and below "4,766,316", insert
-- 4,786,817 A   11/1988   Boissevain et al -- and
-- 5,276,327 A   1/1994  Bossen et al --;
FOREIGN PATENT DOCUMENTS, below "JP 59-57107   4/1984", insert
-- DE    3631652 A1     3/1998 --

Signed and Sealed this

Twenty-fifth Day of May, 2004

JON W. DUDAS
*Acting Director of the United States Patent and Trademark Office*